US012601739B2

(12) United States Patent
Jiang et al.

(10) Patent No.: US 12,601,739 B2
(45) Date of Patent: Apr. 14, 2026

(54) ANTIBODY DETECTION TEST STRIP OF INTEGRATING PRIMARY SCREENING AND DIAGNOSIS OF SHEEP BRUCELLOSIS

(71) Applicant: Institute of Animal Sciences, Chinese Academy of Agricultural Sciences, Beijing (CN)

(72) Inventors: Hui Jiang, Beijing (CN); Jiabo Ding, Beijing (CN); Yu Feng, Beijing (CN)

(73) Assignee: Institute of Animal Sciences, Chinese Academy of Agricultural Sciences, Beijing (CN)

( * ) Notice: Subject to any disclaimer, the term of this patent is extended or adjusted under 35 U.S.C. 154(b) by 442 days.

(21) Appl. No.: 18/130,005

(22) Filed: Apr. 3, 2023

(65) Prior Publication Data

US 2024/0044891 A1     Feb. 8, 2024

(30) Foreign Application Priority Data

Aug. 2, 2022    (CN) ......................... 202210920912.5

(51) Int. Cl.
*G01N 33/569*          (2006.01)
*G01N 33/58*          (2006.01)
(52) U.S. Cl.
CPC ..... *G01N 33/56911* (2013.01); *G01N 33/585* (2013.01)
(58) Field of Classification Search
CPC ............... Y02A 40/70; G01N 2469/20; G01N 2333/23; G01N 33/6854; G01N 33/587; G01N 33/577; G01N 33/585; G01N 33/558; G01N 33/54306; G01N 33/532; G01N 33/56911
See application file for complete search history.

(56) References Cited

U.S. PATENT DOCUMENTS

2016/0223536 A1*    8/2016    Johnson ............. G01N 21/6428

FOREIGN PATENT DOCUMENTS

| CN | 101055273 A | 10/2007 |
| CN | 101055274 A | 10/2007 |
| CN | 101441215 A | 5/2009 |
| CN | 103149356 A | 6/2013 |

OTHER PUBLICATIONS

Dandan (2019 Asia-Pacific Conference on Clinical Medicine and Public Health (CMPH 2019). (Year: 2019).*

* cited by examiner

*Primary Examiner* — Jana A Hines
(74) *Attorney, Agent, or Firm* — Hemisphere Law, PLLC

(57)          ABSTRACT

An antibody detection test strip of integrating primary screening and diagnosis of sheep brucellosis includes: a test strip 1 of primary screening and a test strip 2 of diagnosis, each including a PVC base plate, a sample pad, a colloidal gold labeled pad, a nitrocellulose membrane and an absorbent pad. For the test strip 1, the colloidal gold labeled pad is coated with colloidal gold labeled *Brucella* LPS and mouse anti Flag monoclonal antibody, and test and control lines are respectively coated with a *Brucella* monoclonal antibody M4 and a sheep anti-mouse IgG antibody. For the test strip 2, the colloidal gold labeled pad, and test and control lines are respectively coated with a colloidal gold labeled *Brucella* LPS, a rabbit anti-sheep IgG antibody and a *Brucella* monoclonal antibody M4. When in use, a serum is dripped into its sample-loading hole, and brucellosis determination can be made on site according to results presented by the test strips 1 and 2.

6 Claims, 2 Drawing Sheets

Sample loading hole

T          T

C          C 1          2

Y Antibody to be test          Y Mouse anti Flag mAb          Y *Brucella* mAb          Y Sheep anti mouse antibody

*Brucella* antigen          Colloidal gold labeled *Brucella* antigen          Colloidal gold labeled Mouse anti Flag mAb Sample pad          Nitrocellulose membrane          Absorbent pad
PVC base plate Colloidal gold labeled pad          T line          C line

ANTIBODY DETECTION TEST STRIP OF INTEGRATING PRIMARY SCREENING AND DIAGNOSIS OF SHEEP BRUCELLOSIS

TECHNICAL FIELD

The invention relates to the field of biological product detection technologies, and particularly to an antibody detection test strip of integrating primary screening and diagnosis of sheep brucellosis.

BACKGROUND

The brucellosis is a kind of chronic, multiorgan-damaging zoonotic infectious disease caused by *Brucella*, which seriously threatens life and health of human and many kinds of animals. Such disease not only has serious harm to reproductive and productive performances of animals, but more importantly, human infected with *Brucella* are often difficult to be cured, thus causing a serious public health problem. Therefore, in a *Brucella*-endemic country, the elimination of brucellosis has been one of the most important goals of a public health program. In the year 2016, the world health organization (WHO) regarded the brucellosis as "the most widespread zoonotic disease in the world, but also one of seven important infectious diseases that are most easily neglected by people".

China is a country with high burden of brucellosis, and according to an animal epidemic situation published in the "Official Veterinary Bulletin" of the Ministry of Agriculture and Rural Affairs, a situation of reported new cases of cattle and sheep in China in the past six years has been analyzed as that new cases of brucellosis reported in each year account for 88.2% of total reported cases of all diseases of cattle and sheep, while a total number of reported new cases of other eight relatively important epidemic diseases accounts for only 11.2%. Based on a breeding scale of cattle and sheep released by the National Bureau of Statistics and the positive rate base of brucellosis published by the China Animal Disease Control Center, it is estimated that three kinds of losses including litter size reduction, milk production reduction and animal utilization parity reduction caused by animal brucellosis alone reached 77 billion RMB in 2019, and the three losses in 2021 exceeded 83 billion RMB.

Human infection with brucellosis is caused by contact with domestic animals infected with brucellosis or their products, and a serious epidemic situation of brucellosis in domestic animals in China leads to a serious epidemic situation of human brucellosis. Statistics on the official website of the National Health Commission in 2021 reported that there were 69,767 new cases of human brucellosis which was the highest numbers in China, in history. As internationally recognized calculation that an actual number of cases is 10 to 25 times of the number of reported cases, the actual number of new cases of human brucellosis in China in 2021 has reached an astonishing 690,000 to 1,720,000, and thus losses of health and productivity are incalculable.

The brucellosis is a very serious threat to public health and animal husbandry production, and thus it is urgent to prevent and control the brucellosis. Practices of brucellosis prevention and control in the world have repeatedly proved that well controlling the animal brucellosis is the most economical and effective strategy to prevent and control the human brucellosis. "Detection-elimination" is a basic strategy of brucellosis prevention and control in the world, and its core point is to be able to diagnose accurately and rapidly, and to achieve rapid and accurate diagnosis.

With the progress of science and technology, serological detection methods of the animal brucellosis have been continuously improved. Traditional agglutination assays (such as Rose-Bengal antigen plate agglutination test, standard tube antigen agglutination test, and milk ring agglutination test) have gradually been replaced by new detection technologies such as enzyme linked immunosorbent assay (ELISA) and fluorescence polarization assay (FPA), with higher sensitivity and specificity. In serological detections of brucellosis, a complement fixation test (CFT) is considered to be superior to other methods in specificity, and is often used for qualitative detection of positive or suspicious cases detected out by tube antigen agglutination assay and the Rose-Bengal antigen plate agglutination assay. The complement fixation test has always been considered as the most effective diagnostic method for brucellosis, but preparations of a complement and a hemolysin required by the complement fixation test are difficult, and the assay operation is cumbersome, and thus it is difficult to be widely used in clinical practices.

The ELISA is a diagnostic method with a comparable effect as the CFT, which is easy to operate, has high sensitivity and good specificity, and can complete detections of a large number of samples at one time, and therefore it can be used not only as a screening assay for animal group quarantine, but also as a diagnostic assay. The ELISA can be applied not only to a detection of serum antibody, but also to a detection of antibody in a milk sample. At present, ELISA methods for detection of brucellosis include two kinds, i.e., an indirect ELISA (iELISA) and a competitive ELISA (cELISA). The iELISA is mainly used to detect an IgG (abbreviation of immunoglobulin G) type antibody in a serum, and a detection result thereof is basically equivalent to that of the CFT method, and thus the iELISA can be used as a diagnostic method for brucellosis. The cELISA requires the use of a *Brucella* specific monoclonal antibody to compete with a brucellosis specific antibody in a serum, and thus can detect both IgG and IgM (abbreviation of immunoglobulin M) type antibodies in the serum. Because the IgM type antibody indicates an early stage of acute infection (infection is not yet clear), and IgM has a certain degree of non-specificity, and therefore the cELISA for simultaneous detection of IgG and IgM can be used as a primary screening method for brucellosis in clinic. The detection methods for brucellosis as described above have their own characteristics, but a common defect thereof is that the above assays must be done in the laboratory. In general, serums are separated first, and then laboratory assays are carried out as per operating procedures of the respective detection methods.

PURPOSE OF INVENTION

For the detection of brucellosis, the most urgent thing at present is to realize a rapid and accurate detection on site, which is particularly important for cross-regional allocations of cattle and sheep. An immune colloidal gold technology overcomes the defect that the ELISA assays need to be carried out in the laboratory, and can directly drip, after blood collection, the blood into a sample-loading hole of a colloidal gold test strip, and thus can judge whether the blood is infected by brucellosis on site. Although there have been invention patent applications report about *Brucella* colloidal gold diagnostic test strips, they still have their own shortcomings. Although some commercial test strips have been used for the detection of brucellosis, test results thereof are generally only for reference, and laboratory diagnosis is still required for confirmation. Aiming at the practical difficulty of clinical diagnosis, an embodiment of the invention integrates two colloidal gold detection test strips with different detection principles, one of the test strips is used to simultaneously detect IgG and IgM in a sheep blood to be tested through a principle of *Brucella* monoclonal antibody competitive method, and the other one test strip is used to only detect IgG in the sheep blood to be tested through a principle of indirect method. The two test strips share one sample-loading hole and are placed in a same shell frame to form a test integral structure. When in use, a serum to be tested as a sample to be tested only needs to be dripped into its sample-loading hole, and the sample to be tested can be determined to be negative, positive or suspicious of brucellosis according to band states presented by the two test strips, so that the technical problem of accurate diagnosis of brucellosis, which puzzles the clinical frontline of Brucellosis for a long time, can be solved.

The invention may achieve advantages of simple and rapid operation, easy judgment of results, and no need of any additional instrument and equipment, and thus is suitable for rapid clinical diagnosis.

SUMMARY

An embodiment of the invention builds a colloidal gold test strip (test strip 1) for simultaneous detection of IgG and IgM against *Brucella* in an animal serum by a screened *Brucella* high-affinity monoclonal antibody (i.e., M4 strain), then integrates with a built colloidal gold test strip (test strip 2) for detection of a *Brucella* IgG type antibody in a sheep serum, and then dispose the two test strips into a same shell frame to form a new test unit. In the test unit, detection thresholds of the two test strips are precisely controlled to the same level as that of a *Brucella* complement fixation test (CFT) to thereby ensure consistent detection sensitivities. When in use, a serum to be tested as a sample to tested is dripped into a sample-loading hole, and then a brucellosis negative, positive or suspicious determination can be made on the basis of results presented by the two colloidal gold test strips. A purpose of the invention is to provide a convenient, accurate and rapid on-site diagnostic method for sheep brucellosis.

Technical solutions of embodiments of the invention are as follows.

1. An antibody detection test strip of integrating primary screening and diagnosis of sheep brucellosis, including: a primary screening test strip (test strip 1) and a diagnosis test strip (test strip 1) both arranged in a same shell frame to form a new test unit. Each of the test strip and the test strip 2 includes a polyvinyl chloride (PVC) base plate, a sample pad, a colloidal gold labeled pad, a nitrocellulose membrane and an absorbent pad. Moreover, the antibody detection test strip of integrating primary screening and diagnosis of sheep brucellosis is configured (i.e., structured and arranged) to, when in use, be dripped with a serum to be tested as a sample to be tested into a sample-loading hole thereof and present results by the test strip 1 and the test strip 2 to allow making a brucellosis negative, positive or suspicious determination for the sample to be tested. In other words, when in use, a serum to be tested as a sample to be tested is dripped into a sample-loading hole thereof, and a brucellosis negative, positive or suspicious determination for the sample to be tested can be made according to results presented by the test strip 1 and the test strip 2.

2. The colloidal gold labeled pad of the test strip 1 is coated with a colloidal gold labeled *Brucella* lipopolysaccharide (LPS) and a colloidal gold labeled mouse anti Flag monoclonal antibody, a test line of the test strip 1 is coated with a *Brucella* monoclonal antibody M4, and a control line of the test strip 1 is coated with a sheep anti-mouse immunoglobulin G (IgG) antibody.

3. The colloidal gold labeled pad of the test strip 2 is coated with a colloidal gold labeled *Brucella* LPS, a test line of the test strip 2 is coated with a rabbit anti-sheep IgG antibody, and a control line of the test strip 2 is coated with a *Brucella* monoclonal antibody M4.

4. A preparation method of the colloidal gold labeled *Brucella* LPS includes:

(1) centrifuging an inactivated *Brucella* suis strain 2 (S2) suspension with a bacterial content no less than $1\times10^{10}$ CFU/mL at 10,000 g for 20 minutes and collecting a precipitate, extracting a *Brucella* LPS by a hot phenol-water method, dialyzing extracted supernatant with distilled water and a dialysis bag overnight, and collecting a content in the dialysis bag to obtain a purified LPS; and (2) taking 10 mL of colloidal gold solution into a centrifuge tube and adding a 20-60 µL of 0.1 mol/L (M) $K_2CO_3$ solution to make a pH value approach 7.5, adding 140 µL of prepared LPS solution into the colloidal gold solution and then incubating at room temperature for 20 minutes, then adding 0.02 g of bovine serum albumin (BSA) to give a final concentration of 0.2%, mixing evenly, centrifuging at 10,000 r/min for 40 minutes at 4° C., discarding a supernatant thereof, and finally redissolving a precipitate thereof with 2 mL of 0.02 M phosphate buffer to obtain the colloidal gold labeled *Brucella* LPS.

5. A preparation method of the *Brucella* monoclonal antibody M4 includes:

*Brucella* suis S2 inactivated bacterial solution ($1\times10^{10}$ CFU/mL) as an antigen to immunize a mouse, performing a booster immunization after three times of routine immunizations, taking spleen cells and SP2/0 myeloma cells of the mouse 72-96 hours after the booster immunization for cell fusion, collecting a supernatant of hybridoma cells, then using a LPS-coated 96-well microplate to do an indirect ELISA to screen a positive hybridoma cell strain M4 that has strong reaction with the *Brucella* LPS but almost has no reaction with LPS of *Escherichia coli* O157 strain and *Yersinia enterocolitica* O9 strain, and amplification-culturing and purifying the positive hybridoma cell strain M4 as screened to thereby obtain the *Brucella* monoclonal antibody M4.

The deposits were made and accepted under the Budapest Treaty and applicant avers under 37 CFR § 1.808 (a) that the deposit was made under conditions that assure that:

(1) Access to the deposit will be available during pendency of the patent application making reference to the deposit to one determined by the Director to be entitled thereto under § 1.14 and 35 U.S.C. § 122, and (2) Subject to paragraph (b) of this section, all restrictions imposed by the depositor on the availability to the public of the deposited material will be irrevocably removed upon the granting of the patent.

6. Detection sensitivities of the test strip 1 and the test strip 2 both are 50 IU/mL determined by quantification using a brucellosis positive standard serum (sheep, with a content of 1,000 IU/mL).

7. A method for quantification of the detection sensitivities of the test strip 1 and the test strip 2 includes:

diluting the sheep brucellosis positive standard serum with physiological saline at four different dilution ratios of 1:10, 1:20, 1:40 and 1:80, namely contents of serum antibody being 100 IU/mL, 50 IU/mL, 25 IU/mL and 12.5 IU/mL; dripping positive serums with the respective dilution ratios each two drops (100 μL) into respective the sample-loading holes, and reading results within 2~5 minutes; and determining results of detection sensitivities of the test strip 1 and the test strip 2 as that: for the sheep brucellosis positive standard serum diluted as 1:20, namely 50 IU/mL, it is determined as positive because that a test line of the test strip 1 presents no band but a control line of the test strip 1 presents a band, and a test line and a control line of the test strip 2 each present a band; and for the sheep brucellosis positive standard serum diluted as per the dilution ratio of 1:40, namely 25 IU/mL, it is determined as negative because that the test line and the control line of the test strip 1 each present a band, and the test line of strip 2 presents no band but the control line of strip 2 presents a band.

8. When the antibody detection test strip of integrating primary screening and diagnosis of sheep brucellosis in use, what are performed as follows:

(1) Sample processing: taking whole blood of an animal, and separating a serum being clear and free of hemolysis;

(2) Operation method: dripping two drops (100 μL) of the serum into the sample-loading hole, and reading a result within 2-5 minutes; and (3) Criteria of determination: determining as brucellosis negative (−) when a test line and a control line of the test strip 1 each present a band, and a test line of the test strip 2 presents no band but a control line of the test strip 2 presents a band; determining as brucellosis positive (+) when the test line of the test strip 1 presents no band but the control line of the test strip 1 presents a band, and the test line and the control line of the test strip 2 each present a band; determining as brucellosis suspicious (±) when the test line of the test strip 1 presents no band but the control line of the test strip 1 presents a band, and the test line of the test strip 2 presents no band but the control line of the test strip 1 presents a band; or, determining as invalid when the control line of each of the test strip 1 and the test strip 2 presents no band.

Beneficial effects of the embodiments of the invention are as follows.

The embodiments of the invention integrate a primary screening test strip based on a competitive method with a diagnosis test strip based on an indirect method, to achieve an on-site rapid and accurate diagnostic method of sheep brucellosis. An advantage of the embodiments of the invention is that detection/test sensitivities of the primary screening test strip based on the competitive method and the diagnosis test strip based on the indirect method are quantified through a sheep brucellosis positive standard serum, so that the detection sensitivities of the two test strips are consistent with a detection sensitivity of a gold standard CFT method for brucellosis diagnosing, and thereby the accuracy is improved. Under the condition of the same detection sensitivities, contents of Brucella specific antibodies IgG and IgM in a serum sample are tested by the two test strips independently, thereby achieving the purpose of rapidly determining suspicious sheep, positive sheep or negative sheep of brucellosis on site.

DETAILED DESCRIPTION OF EMBODIMENTS

Figures 1, 2:
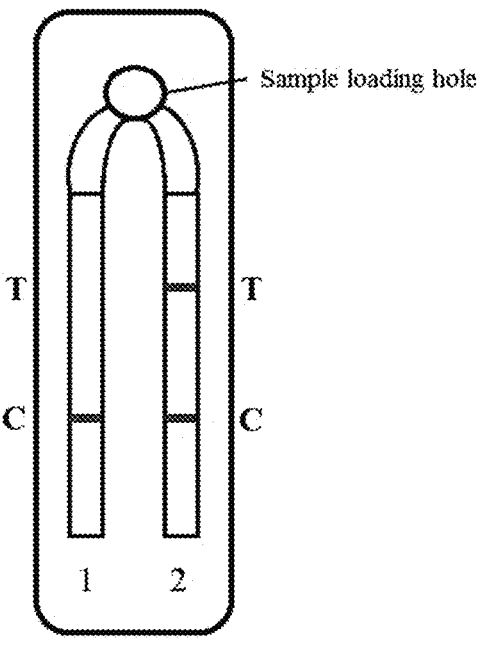
FIG. 1 illustrates a schematic structural view of antibody detection test strip of integrating primary screening and diagnosis of sheep brucellosis according to an embodiment of the invention.
FIG. 2 illustrates a schematic diagram of showing a structure and a working principle of a test strip 1.

An embodiment of the invention builds an antibody detection test strip of integrating primary screening and diagnosis of sheep brucellosis.

A core of the antibody detection test strip is that two colloidal gold test strips with different detection principles are integrated together, i.e., the core is composed of a primary screening test strip (test strip 1) based on a competitive method and a diagnosis test strip (test strip 2) based on an indirect method. The test strip 1 and the test strip 2 each independently include a sample pad, a colloidal gold labeled pad, a nitrocellulose membrane and an absorbent pad. In the test strip 1, the colloidal gold labeled pad is coated with a colloidal gold labeled Brucella lipopolysaccharide (LPS) and a colloidal gold labeled mouse anti Flag monoclonal antibody (abbreviated as mAb), a test line is coated with a Brucella monoclonal antibody M4, and a control line is coated with a sheep anti-mouse IgG antibody. In the test strip 2, the colloidal gold labeled pad is coated with a colloidal gold labeled Brucella LPS, a test line is coated with a rabbit anti-sheep IgG antibody, and a control line is coated with a Brucella monoclonal antibody M4. A brucellosis positive standard serum (i.e., sheep, with a content of 1,000 IU/mL) is employed to precisely control detection/test sensitivities of the test strip 1 and the test strip 2 to be consistent with that of the Brucella complement fixation test (CFT). When in use, a serum to be tested (as a sample to be tested) is dripped into a sample-loading hole, and then a brucellosis negative, positive, or suspicious determination for the sample to be tested can be made rapidly on-site, on the basis of results presented by the test strip 1 and the test strip 2.

Preparation and test methods of the above-described antibody detection test strip of integrating primary screening and diagnosis of sheep brucellosis provided by some illustrated embodiments of the invention may be implemented as follows.

(1) The colloidal gold labeled pad of each of the test strip 1 and the test strip 2 is coated with the colloidal gold labeled Brucella LPS, and a preparation method is that: ① an inactivated Brucella suis S2 suspension is centrifuged at 10,000 g for 20 min, and then a precipitate is collected; a Brucella LPS is extracted by a hot phenol-water method, an extracted supernatant is dialyzed with distilled water and a dialysis bag overnight, and a content in the dialysis bag is collected to thereby obtain a purified LPS. ② 10 mL of colloidal gold solution is taken into a centrifuge tube, and an appropriate amount (e.g., 20-60 μL) of 0.1 M $K_2CO_3$ solution then is added to make the pH value be about 7.5; 140 μL of prepared LPS solution subsequently is added into the colloidal gold solution and incubated for 20 min at room temperature; 0.02 grams of bovine serum albumin (BSA) then is added to give a final concentration of 0.2% and mixed fully; then is refrigerated at 10,000 r/min for 40 min at 4° C., and then a supernatant thereof is discarded; and finally a precipitate thereof is dissolved with 2 mL of 0.02 M phosphate buffer, to obtain the colloidal gold labeled LPS consequently.

(2) The colloidal gold labeled pad of the test strip 1 is labeled with the mouse anti Flag monoclonal antibody, and a preparation method is that: 10 mL of colloidal gold solution is taken into a centrifuge tube, and an appropriate amount of 0.1 M $K_2CO_3$ solution is added to adjust a pH value of the colloidal gold solution to be 7.5; a commercial mouse anti Flag monoclonal antibody then is added as per an amount of 10 μg/mL and incubated for 20 min at room temperature; 0.02 g of BSA subsequently is added to give a final concentration of 0.2% and mixed fully; then is refrigerated at 10,000 r/min for 40 min at 4° C., and then a supernatant thereof is discarded; and finally a precipitate thereof is resuspended with 2 mL of 0.02 M phosphate buffer, and a solution as resuspended is the colloidal gold solution with labeled Flag monoclonal antibody.

(3) The test line of the test strip 1 and the control line of the test strip 2 each are coated with the *Brucella* monoclonal antibody M4, and a preparation method is that: a *Brucella* suis S2 strain inactivated bacterial solution ($1\times10^{10}$ CFU/mL) is used as an antigen to immunize a mouse, and a booster immunization is carried out after three times of routine immunizations; spleen cells and SP2/0 myeloma cells of the mouse are taken 72 to 96 hours after the booster immunization for cell fusion; a supernatant of hybridoma cells then is collected, and a LPS-coated microplate is used to do an indirect enzyme-linked immunosorbent assay to screen a positive hybridoma cell strain M4 that has strong reaction with LPS of *Brucella* but almost have no reaction with LPS of *Escherichia coli* O157 strain and *Yersinia enterocolitica* O9 strain, and the screened positive hybridoma cell strain M4 is amplification-cultured and purified to thereby obtain the *Brucella* monoclonal antibody M4. Moreover, a dilution of 1:200 is made with a membrane-marking coating solution, and then is dispensed onto locations of the test line of the test strip 1 and the control line of the test strip 2 as per 0.1 μL/mm by membrane-marking equipment, and fixed.

(4) The control line of the test strip 1 is coated with the sheep anti-mouse IgG antibody, and a preparation method is that: a commercial sheep anti-mouse IgG antibody is diluted with a membrane-marking coating solution to 0.5 mg/mL, and then dispensed onto the control line of the test strip 1 as per 0.1 μL/mm by membrane-marking equipment, and fixed.

(5) The test line of the test strip 2 is coated with the rabbit anti-sheep IgG antibody, and a preparation method is that: a commercial rabbit anti-sheep IgG antibody is diluted with a membrane-marking coating solution to 1 mg/mL, and then dispensed onto the test line of the test strip 2 as 0.1 μL/mm by membrane-marking equipment, and fixed.

(6) A quantitative method for detection sensitivities of the test strip 1 and the test strip 2 is that: a sheep brucellosis positive standard serum is diluted with physiological saline at four different dilution ratios of 1:10, 1:20, 1:40 and 1:80 for later use, that is, contents of serum antibody are 100 IU/mL, 50 IU/mL, 25 IU/mL and 12.5 IU/ml, respectively; two drops of positive serum (100 μL) with each of the dilution ratios are added into the sample-loading hole, and results are read within 2 to 5 min; and results of detection sensitivities of the test strip 1 and the test strip 2 are determined as that: for the sheep brucellosis positive serum standard diluted as per 1:20 (50 IU/mL), the test line of the test strip 1 presents no band but the control line of the test strip 1 presents a band, the test line and the control line of the test strip 2 each present a band, and thus it is determined as positive; and for the sheep brucellosis positive serum standard diluted as 1:40 (25 IU/mL), the test line and the control line of the test strip 1 each present a band, the test line of the test strip 2 presents no band but the control line of the test strip 2 presents a band, and thus it is determined as negative.

(7) The antibody detection test strip of integrating primary screening and diagnosis of sheep brucellosis, when in use, what are carried out as follows: ① sample processing: taking whole blood of an animal (e.g., sheep) and separating a serum, and the serum should be clear and free of hemolysis; ② operation method: dropwise dripping two drops of the serum (100 μL) into the sample-loading hole and reading results within 2 to 5 min; ③ criteria of determination: when the test line and the control line of the test strip 1 each present a band, and the test line of the test strip 2 presents no band but the control line of the test strip 2 presents a band, it is determined as brucellosis negative (−); when the test line of the test strip 1 presents no band but the control line of the test strip 1 presents a band, and the test line and the control line of the test strip 2 each present a band, it is determined as brucellosis positive (+); when the test line of the test strip 1 presents no band but the control line of the test strip 1 presents a band, and the test line of the test strip 2 presents no band but the control line of the test strip 2 presents a band, it is determined as brucellosis suspicious (±); and when the control line of any one of the test strip 1 and the test strip 2 presents no band, it is determined as invalid.

A test principle of some illustrated embodiments of the invention is as follows.

When a sample containing a *Brucella* antibody flows through the colloidal gold labeled pad of the test strip 1 from the sample-loading hole, the *Brucella* LPS-colloidal gold label on the colloidal gold labeled pad binds with the *Brucella* antibody, and continues flowing through the test line, since the *Brucella* LPS-colloidal gold label has bound with the *Brucella* antibody in the sample and thus cannot bind to the monoclonal antibody M4 of the test line any more, thereby no band is displayed. Afterwards, when continues flowing through the control line, the mouse anti Flag monoclonal antibody-colloidal gold label binds with the sheep anti-mouse IgG antibody, thereby a purplish red band is displayed. Meanwhile, when the sample containing the *Brucella* antibody flows through the colloidal gold labeled pad of the test strip 2 from the sample-loading hole, the *Brucella* LPS-colloidal gold label on the colloidal gold labeled pad binds with the *Brucella* antibody, and continues flowing through the test line to bind with the rabbit anti-sheep IgG antibody and thereby form a complex of *Brucella* LPS-colloidal gold label-*Brucella* antibody-rabbit anti-sheep IgG antibody, so that a purplish red band is displayed; afterwards, continues flowing through the control line, *Brucella* LPS-colloidal gold label not bound with the *Brucella* antibody in the sample binds with the *Brucella* monoclonal antibody M4 coating the control line, and thus a purplish red band is displayed.

If a sample is without containing the *Brucella* antibody, when the sample flows through the colloidal gold labeled pad of the test strip 1, it cannot bind with the *Brucella* LPS-colloidal gold label on the colloidal gold labeled pad, continues flowing through the test line, the *Brucella* LPS-colloidal gold label binds with the monoclonal antibody M4 on the test line, thereby displaying a purplish red band; afterwards, continues flowing through the control line, the mouse anti Flag monoclonal antibody-colloidal gold label binds with the sheep anti-mouse IgG antibody, thereby displaying a purplish red band. Meanwhile, when the sample flows through the colloidal gold labeled pad of the test strip 2 from the sample-loading hole, it cannot bind with the *Brucella* LPS-colloidal gold label on the colloidal gold labeled pad, and continues flowing through the test line, it cannot bind with the rabbit anti-sheep IgG antibody, and thus no purplish red band is displayed; afterwards, continues flowing through the control line, the *Brucella* LPS-colloidal gold label binds with the *Brucella* monoclonal antibody M4 coating the control line, thereby displaying a purplish red band.

EXAMPLES

The following examples are used to further illustrate the invention, but are not intended to limit the invention.

Example 1—Optimization of Conditions for Colloidal Gold Labeling

1. Selection of colloidal gold particle size. Specifically, a 250 mL round bottom flask was taken, 100 mL of distilled water was measured and 1 mL of 1% chloroauric acid solution was added, and then stirred and heated until boiling. Different volumes of 1% sodium citrate aqueous solutions such as 0.5 mL, 1.0 mL, 1.5 mL, 2.0 mL, 2.5 mL were added into the respective chloroauric acid solutions, stirred for mixing evenly, and kept boiling for 10 min. Stopped heating after the 10 min, and after the solution had cooled, distilled water was complementarily added to reach a constant volume of 100 mL, and thereby colloidal gold solutions were prepared. The prepared colloidal gold solutions were stored at 2-8° C. Each of the prepared colloidal gold solutions is dipped by a nickel mesh supporting a membrane, dried naturally and then observed directly in a transmission electron microscope (TEM). An average diameter of 100 colloidal gold protein particles was calculated and $OD_{520\ nm}$ value was determined after each of the colloidal gold solutions was diluted as per 1:20 with a 1×PBS (i.e., 0.01 M phosphate buffered saline) buffer (containing 1% BSA).

2. Determination of optimal pH value for colloidal gold labeling. Specifically, a smooth *Brucella* suis S2 LPS and a commercial Flag monoclonal antibody both being 1 mg/mL and 10 μL were taken and respectively added into colloidal gold solutions each being 1 mL with respective pH values of 7.0, 7.5, 8.0, 8.5 and 9.0, mixed evenly and laid at room temperature for 10-15 min; and afterwards, 20 μL of 10% NaCl solution was added, mixed evenly, and results were observed after being stood at 2-8° C. for 2 hours, and the optimal pH value for colloidal gold labeling was determined consequently.

3. Determination of optimal labeling amount of colloidal gold solution. Specifically, to-be-labeled *Brucella* S2 LPS and commercial Flag monoclonal antibodies both in volumes of 0 μL, 4 μL, 8 μL, 12 μL, 16 μL and 20 μL (each with a concentration of 1 mg/mL) were respectively added into colloidal gold solutions each being 1 mL, and after 45 min at room temperature, 100 μL of 10% NaCl was added and then stood at 2-8° C. for 2 hours, and an increase of 20% on the basis of a minimal added amount of the LPS or the Flag monoclonal antibody on the prerequisite of no change in color of the colloidal gold solution was considered as the optimal labeling amount.

4. Results: (1) the colloidal gold particle size was inversely proportional to the added amount of the sodium citrate (see TABLE 1 below). The colloidal gold prepared by adding 1.5 mL of 1% sodium citrate (generally trisodium citrate) in 100 mL of 0.01% chloroauric acid solution was wine-red in color, the particle sizes were relatively uniform, the average diameter of the colloidal gold particles was about 40 nm (40±4 nm), the $OD_{520\ nm}$ value of the colloidal gold solution was in a range of 0.2-0.3, thus satisfying the requirements. (2) the colloidal gold solutions with the respective pH values of 7.0, 7.5, 8.0, 8.5 and 9.0 were used to label the *brucella* S2 strain LPS and the commercial Flag monoclonal antibodies, and the results showed that two immune colloidal gold solutions were stable and bright in color at pH value of 7.5, so the pH value for colloidal gold labeling was determined to be 7.5. (3) to-be-labeled *brucella* S2 strain LPS and commercial Flag monoclonal antibodies both in volumes of 0 μL, 4 μL, 8 μL, 12 μL, 16 μL and 20 μL (each with a concentration of 1 mg/mL) were respectively added into colloidal gold solutions each being 1 mL, and after 45 min, 100 μL of 10% NaCl was added, and then stood at 2-8° C. for 2 hours. A minimum content corresponding to the wine-red LPS colloidal gold solution without color change is 12 μL, and thus about 20% was increased on this basis, that is, every milliliter of colloidal gold solution contains 14 μL of LPS (1 mg/mL). A minimum content corresponding to the wine-red commercial Flag monoclonal antibody colloidal gold solution without color change is 8 μL, i.e., containing 8 μL of the commercial Flag monoclonal antibody, and thus about 20% was increased on this basis, that is, every milliliter of colloidal gold solution contains 10 μL of the Flag monoclonal antibody.

TABLE 1

Relationships between added amounts of trisodium citrate and colloidal gold particle sizes during colloidal gold preparation

| 0.01% chloroauric acid (mL) | 1% sodium citrate (mL) | color of colloidal gold solution | Diameter of colloidal gold particle | $OD_{520\ nm}$ |
|---|---|---|---|---|
| 100 | 0.5 | purple | 74.5 | 0.49 |
| 100 | 1.0 | purplish red | 60.1 | 0.37 |
| 100 | 1.5 | Wine-red | 40.8 | 0.26 |
| 100 | 2.0 | red | 25.6 | 0.17 |
| 100 | 2.5 | orange | 15.1 | 0.10 |

Figure 3:
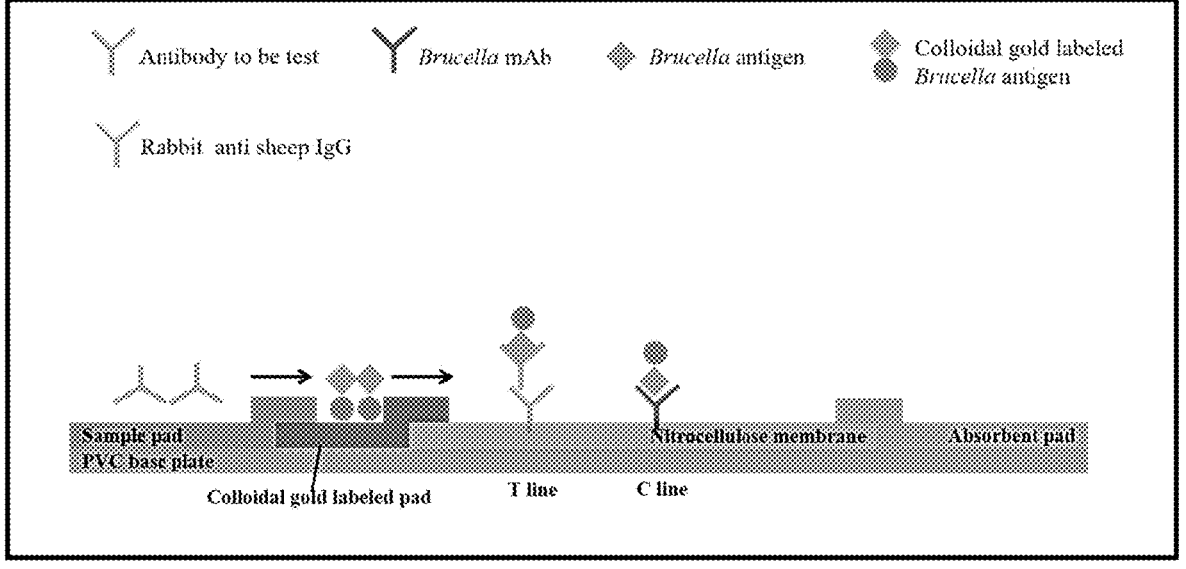
FIG. 3 illustrates a schematic diagram of showing a structure and a working principle of a test strip 2.

Example 2—Structure of Antibody Detection Test Strip of Integrating Primary Screening and Diagnosis of Sheep Brucellosis An antibody detection test strip of integrating primary screening and diagnosis of sheep brucellosis according to this example is shown in FIG. 1, and includes a primary screening test strip (test strip 1) and a diagnosis test strip (test strip 2). Each of the test strip 1 and the test strip 2 includes a sample pad, a colloidal gold labeled pad, a nitrocellulose membrane and an absorbent pad sequentially pasted onto a polyvinyl chloride (PVC) base plate. As illustrated in FIG. 2, the colloidal gold labeled pad of the test strip 1 is coated with a colloidal gold labeled *Brucella* LPS and a colloidal gold labeled mouse anti Flag monoclonal antibody, a test line (T line) of the test strip 1 is coated with a *Brucella* monoclonal antibody M4, and a control line (C line) of the test strip 1 is coated with a sheep anti-mouse IgG antibody. As illustrated in FIG. 3, the colloidal gold labeled pad of the test strip 2 is coated with a colloidal gold labeled *Brucella* LPS, a test line (T line) of the test strip 2 is coated with a rabbit anti-sheep IgG antibody, and a control line (C line) of the test strip 2 is coated with a *Brucella* monoclonal antibody M4.

Example 3—Preparation of Antibody Detection Test Strip of Integrating Primary Screening and Diagnosis of Sheep Brucellosis 1. Preparation of LPS and Colloidal Gold Labeling
    (1) LPS purity determination. Specifically, the lyophilized LPS antigen was taken, weighed, and dissolved with a carbonate buffer (0.05 mol/L, with a pH value of 9.6) to obtain a concentration of 1 mg/mL in absolute mass. Then, it was diluted with sterile physiological saline as per 1:10000, detected with a commercial LPS test kit, a standard curve was drawn, a regression equation of the standard curve was calculated, a sample concentration was calculated according to the $OD_{570\ nm}$ value of the sample, and then purity of the sample was calculated according to a formula that: purity=(LPS measured concentration/1 mg/mL)×100%.
    (2) Colloidal gold labeling LPS. Specifically, 10 mL of colloidal gold solution was taken into a centrifuge tube, and then an appropriate amount of 0.1 M $K_2CO_3$ solution was added to make a pH value thereof be about 7.5. Then, 140 μL of prepared LPS solution was added into the colloidal gold solution, and incubated for 20 min at room temperature. 0.02 g of bovine serum albumin (BSA) subsequently was added to give a final concentration of 0.2%, and mixed fully. Centrifugation then was carried out at 10,000 r/min for 40 min at a condition of 4° C., and then a supernatant thereof was discarded. Finally, a precipitate thereof was redissolved with 2 mL of M phosphate buffer, thereby obtaining the colloidal gold labeled LPS.
2. Preparation of Colloidal Gold Labeled Mouse Anti Flag Monoclonal Antibody
    10 mL of colloidal gold solution was taken into a centrifuge tube, and an appropriate amount of 0.1 M $K_2CO_3$ solution was added to adjust a pH value of the colloidal gold solution to be 7.5. A commercial mouse anti Flag monoclonal antibody then was added as 10 μg/mL, and incubated for 20 min at room temperature. 0.02 g of BSA subsequently was added to give a final concentration of 0.2%, and mixed fully. Centrifugation then was carried out by an ultra-low temperature refrigerated centrifuge at 10,000 r/min for 40 min at 4° C., and then a supernatant thereof was discarded. Finally, a precipitate thereof was resuspended with 0.02 M phosphate buffer, thereby obtaining colloidal gold solution with labeled Flag monoclonal antibody.
3. Preparation of *Brucella* Monoclonal Antibody M4
    A *Brucella* suis S2 inactivated bacterial solution ($1\times10^{10}$ CFU/mL) was used as an antigen to immunize a mouse, and a booster immunization was carried out after three times of routine immunizations. Spleen cells and SP2/0 cells of the mouse were taken 72-96 hours after the booster immunization for cell fusion. A supernatant of hybridoma cells then was collected, and an LPS-coated 96-well microplate was used to do an indirect enzyme-linked immunosorbent assay to screen a positive hybridoma cell strain M4 that has strong reaction with LPS of *Brucella* but almost has no reaction with LPS of *Escherichia coli* O157 strain and *Yersinia enterocolitica* O9 strain, and the screened positive hybridoma cell strain M4 then was amplification-cultured and purified, thereby obtaining the monoclonal antibody M4.
4. Preparation and Assembly of Test Strip 1
    (1) Preparation of colloidal gold labeled pad. Specifically, the prepared colloidal gold labeled LPS solution and the colloidal gold labeled Flag monoclonal antibody solution were mixed as per a ratio of 1:1, and then were sprayed evenly onto a treated gold pad as per 0.2 μL/mm by a gold dispenser and dried in a constant-temperature drying oven for 16 hours at 37° C., for later use.
    (2) Preparation of test line (T line) and control line (C line). Specifically, the *Brucella* monoclonal antibody M4 was diluted with a membrane-marking coating solution as per a dilution ratio of 1:200, and then dispensed onto a location of the test line (T line) of a nitrocellulose membrane by membrane-marking equipment as per 0.1 μL/mm. Moreover, a sheep anti-mouse IgG antibody was diluted with a membrane-marking coating solution to 0.5 mg/mL, and then dispensed onto a location of the control line (C line) of the nitrocellulose membrane by membrane-marking equipment as per 0.1 μL/mm, dried in a constant-temperature drying oven for 16 hours at 37° C., and then dry stored at room temperature.
    (3) Assembly of test strip 1. Specifically, the nitrocellulose membrane was pasted onto a corresponding location of a PVC plate, and then a sample pad, the colloidal gold labeled pad and an absorbent paper were sequentially pasted onto corresponding locations of the PVC plate. In particular, the colloidal gold labeled pad was in partial contact with the nitrocellulose membrane, e.g., a portion of about 1-2 mm of the colloidal gold labeled pad was contacted with the nitrocellulose membrane; and the absorbent paper was in partial contact with the nitrocellulose membrane, e.g., a portion of about 2-3 mm of the absorbent paper was contacted with the nitrocellulose membrane. Afterwards, a strip cutter was used to cut the resultant structure into small strips each with a width of 3 mm, thereby obtaining test strips 1.
5. Preparation and Assembly of Test Strip 2
    (1) Preparation of colloidal gold labeled pad. Specifically, the prepared colloidal gold labeled LPS solution was sprayed evenly onto a treated gold pad as per 0.2 μL/mm by a gold dispenser, and then dried in a constant-temperature drying oven for 16 hours at 37° C., for later use.

(2) Preparation of test line (T line) and control line (C line). Specifically, a commercial rabbit anti-sheep IgG antibody was diluted with a membrane-marking coating solution to 1 mg/mL, and then dispensed onto a location of the test line (T line) of a nitrocellulose membrane by membrane-marking equipment as per 0.1 μL/mm. Moreover, the *Brucella* monoclonal antibody M4 was diluted with a membrane-marking coating solution as per a dilution ratio of 1:200, and then dispensed onto a location of the control line (C line) of the nitrocellulose membrane by membrane-marking equipment as per 0.1 μL/mm, dried in a constant-temperature drying oven for 16 hours at 37° C., and then dry stored at room temperature.

(3) Assembly of test strip 2. Specifically, the nitrocellulose membrane was pasted onto a corresponding location of a PVC plate, and then a sample pad, the colloidal gold labeled pad and an absorbent paper were sequentially pasted onto corresponding locations of the PVC plate. In particular, the colloidal gold labeled pad was in partial contact with the nitrocellulose membrane, e.g., a portion of about 1-2 mm of the colloidal gold labeled pad was contacted with the nitrocellulose membrane; and the absorbent paper was in partial contact with the nitrocellulose membrane, e.g., a portion of about 2-3 mm of the absorbent paper was contacted with the nitrocellulose membrane. Afterwards, a strip cutter was used to cut the resultant structure into small strips each with a width of 3 mm, thereby obtaining test strips 2.

6. Assembly of Antibody Detection Test Strip of Integrating Primary Screening and Diagnosis of Sheep Brucellosis The test strip 1 and the test strip 2 were respectively placed in corresponding positions of a test card cover plate, so that the sample pads of the test strip 1 and the test strip 2 were connected with each other; and then upper and lower cover plates of test card are fixed together to obtain an antibody detection test strip of integrating primary screening and diagnosis of sheep brucellosis.

Example 4—Sensitivity Test of the Antibody Detection Test Strip of Integrating Primary Screening and Diagnosis of Sheep Brucellosis 1. A positive standard serum of sheep brucellosis was diluted with physiological saline at four different dilution ratios of 1:10, 1:20, 1:40 and 1:80, for later use, that is, contents of serum antibody were 100 IU/mL, 50 IU/mL, 25 IU/mL and 12.5 IU/mL, for later use.

2. Positive serums with the different dilution ratios were taken and dropwise dripped into respective sample-loading holes each with two drops (100 μL), and then results were determined after samples flow through the respective test and control lines. Criteria of determination was that: when the test line and the control line of the test strip 1 each display a band, and the test line of the test strip 2 displays no band but the control line of the test strip 2 displays a band, determining as brucellosis negative (−); when the test line of the test strip 1 displays no band but the control line of the test strip 1 displays a band, and the test line and the control line of the test strip 2 each display a band, determining as brucellosis positive (+); when the test line of the test strip 1 displays no band but the control line of the test strip 1 displays a band, and the test line of the test strip 2 displays no band but the control line of the test strip 2 displays a band, determining as brucellosis suspicious (±); when the control line of any one of the test strip 1 and the test strip 2 displays no band, determining as invalid.

3. Results of sensitivity test of the antibody detection test strip are shown in TABLE 2 below. The results showed that the sensitivity of the antibody detection test strip of integrating primary screen and diagnosis of sheep brucellosis was as follows: the positive standard serum of sheep brucellosis diluted as per the dilution ratio of 1:20 (i.e., 50 IU/mL) was determined as positive, and the positive standard serum of sheep brucellosis diluted as per the dilution ratio of 1:40 (i.e., 25 IU/mL) was determined as negative.

TABLE 2

Results of sensitivity test of antibody detection test strip of integrating primary screen and diagnosis of sheep brucellosis

| | Contents of serum antibody of respective dilution ratios | | | |
| --- | --- | --- | --- | --- |
| Test strip | 100 IU/mL | 50 IU/mL | 25 IU/mL | 12.5 IU/mL |
| Test strip 1 | T(−), C(+) | T(−), C(+) | T(+), C(+) | T(+), C(+) |
| Test strip 2 | T(+), C(+) | T(+), C(+) | T(−), C(+) | T(−), C(+) |
| Result | Positive | Positive | Negative | Negative |

Notes:
T(+) represents the test line presents a band, T(−) represents the test line presents no band, C(+) represents the control line presents a band, C(−) represents the control line presents no band.

Example 5—Sensibility and Specificity Tests of Antibody Detection Test Strip of Integrating Primary Screen and Diagnosis of Sheep Brucellosis 1. For 402 pieces of sheep serum samples collected in laboratory from the year 2018 to the year 2021, 189 pieces of brucellosis positive serums were tested as positive by test methods of a Rose-Bengal plate agglutination test (RBT), a standard tube agglutination test (SAT), a complement fixation test (CFT), a competitive enzyme linked immunosorbent assay (cELISA) and an indirect enzyme linked immunosorbent assay (iELISA), and the other 213 pieces of brucellosis negative serums were tested as negative by the above test methods.

2. Each of the above serum samples about 100 μL was taken and dropwise dripped into a sample-loading hole. Results were determined after the serum samples flow through the test and control lines of respective test strips 1 and 2. Criteria of determination was that: when the test line and the control line of the test strip 1 each display a band, and the test line of the test strip 2 displays no band but the control line of the test strip 2 displays a band, determining as brucellosis negative (−); when the test line of the test strip 1 displays no band but the control line of the test strip 1 displays a band, and the test line and the control line of the test strip 2 each display a band, determining as brucellosis positive (+); when the test line of the test strip 1 displays no band but the control line of the test strip 1 displays a band, and the test line of the test strip 2 displays no band but the control line of the test strip 2 displays a band, determining as brucellosis suspicious (±); when the control line of any one of the test strip 1 and the test strip 2 displays no band, determining as invalid.

3. Results of sensibility test of the antibody detection test strip were that: the 189 pieces of positive serums of sheep brucellosis all are tested as positive, indicating the antibody detection test strip had high sensibility. Results of specificity test of the antibody detection test strip were that: the 213 pieces of negative serums of sheep brucellosis all are tested as negative, indicating the antibody detection test strip had good specificity.

Example 6—Clinical Sample Validation Test of Antibody Detection Test Strip of Integrating Primary Screen and Diagnosis of Sheep Brucellosis 1. 657 pieces of clinical sheep serum samples collected in laboratory from the year 2018 to the year 2021 were tested by both the complement fixation test (CFT) and the antibody detection test strip, and then a coincidence rate between test results of the antibody detection test strip and the test results of the CFT was calculated.
2. A result is shown in TABLE 3 below. The antibody detection test strip tested the 657 pieces of clinical sheep serum samples, and the test results thereof had a coincidence rate of 98.02% with the gold standard complement fixation test (CFT) of serological diagnosis of brucellosis.

TABLE 3

Result of clinical sample validation test of antibody detection test strip of integrating primary screen and diagnosis of sheep brucellosis

| | | complement fixation test (CFT) | | | |
| | | Posi-tive sample number | Nega-tive sample number | Suspi-cious sample number | Total |
|---|---|---|---|---|---|
| Antibody detection test strip of integrating primary screening and diagnosis of sheep brucellosis | Positive sample number | 154 | 4 | 3 | 161 |
| | Negative sample number | 1 | 488 | 0 | 489 |
| | Suspicious sample number | 2 | 3 | 2 | 7 |
| Total | | 157 | 495 | 5 | 657 |

Coincidence rate (154 + 488 + 2)/657 × 100% = 98.02%

The above description is only preferred embodiments of the invention. It should be pointed out that those skilled in the art can make several improvements and modifications without departing from the principle of the invention, and these improvements and modifications should also be considered as the scope of protection of the invention.

What is claimed is:

1. An antibody detection test strip of integrating primary screening and diagnosis of sheep brucellosis, comprising: a primary screening test strip (test strip 1) and a diagnosis test strip (test strip 1) both disposed in a same shell frame to form a single test unit;

wherein each of the test strip 1 and the test strip 2 comprises a polyvinyl chloride (PVC) base plate, a sample pad, a colloidal gold labeled pad, a nitrocellulose membrane and an absorbent pad; and the antibody detection test strip of integrating primary screening and diagnosis of sheep brucellosis is configured to, when in use, be dripped with a sheep serum to be tested as a sheep serum sample into a sample-loading hole thereof and present results by the test strip 1 and the test strip 2 to allow making brucellosis negative, positive or suspicious determination for the sheep serum sample;

wherein the colloidal gold labeled pad of the test strip 1 is coated with a colloidal gold labeled *Brucella* LPS and a colloidal gold labeled mouse anti Flag monoclonal antibody, a test line of the test strip 1 is coated with a *Brucella* monoclonal antibody M4, and a control line of the test strip 1 is coated with a sheep anti-mouse immunoglobulin G (IgG) antibody; and wherein the colloidal gold labeled pad of the test strip 2 is coated with a colloidal gold labeled *Brucella* LPS, a test line of the test strip 2 is coated with a rabbit anti-sheep IgG antibody, and a control line of the test strip 2 is coated with a *Brucella* monoclonal antibody M4.

2. The antibody detection test strip of integrating primary screening and diagnosis of sheep brucellosis as claimed claim 1, wherein a preparation method of the colloidal gold labeled *Brucella* LPS comprises:

(1) centrifuging an inactivated *Brucella* strain 2 (S2) suspension with a bacterial content greater than or equal to $1 \times 10^{10}$ colony forming units per milliliter (CFU/mL) at 10,000 g for 20 minutes and collecting a precipitate, extracting a *Brucella* LPS by a hot phenol-water method, dialyzing extracted supernatant with distilled water and a dialysis bag overnight, and collecting a content in the dialysis bag to obtain a purified LPS; and (2) taking 10 milliliters (mL) of colloidal gold solution into a centrifuge tube and adding 20-60 microliters (μL) of 0.1 mol/L (M) $K_2CO_3$ solution to make a pH value be 7.5, adding 140 μL of prepared LPS solution into the colloidal gold solution and then incubating at room temperature for 20 minutes, then adding 0.02 g of BSA to give a final concentration of 0.2%, mixing evenly, centrifuging at 10,000 r/min for 40 minutes at 4° C., discarding a supernatant, and finally dissolving a precipitate with 2 mL of 0.02 M phosphate buffer to obtain the colloidal gold labeled *Brucella* LPS.

3. The antibody detection test strip of integrating primary screening and diagnosis of sheep brucellosis as claimed claim 1, wherein a preparation method of the *Brucella* monoclonal antibody M4 comprises:

using a *Brucella suis* S2 inactivated bacterial solution of $1 \times 10^{10}$ CFU/mL as an antigen to immunize a mouse, performing a booster immunization after three times of routine immunizations, taking spleen cells and SP2/0 cells of the mouse 72-96 hours after the booster immunization for cell fusion, collecting a supernatant of hybridoma cells, then using a LPS-coated 96-well microplate to do an indirect ELISA to screen a positive hybridoma cell strain M4 that has strong reaction with the *Brucella* LPS but almost has no reaction with LPS of *Escherichia coli* O157 strain and *Yersinia enterocolitica* O9 strain, and amplification-culturing and purifying the positive hybridoma cell strain M4 as screened to thereby obtain the *Brucella* monoclonal antibody M4;

wherein the *Brucella suis* S2 (CVCC70502) and the *Escherichia coli* O157 strain (CVCC1489) are available from the national center for veterinary culture collection in China, and the *Yersinia enterocolitica* O9 strain (CMCC52218) is available from the national center for medical culture collections in China.

4. The antibody detection test strip of integrating primary screening and diagnosis of sheep brucellosis as claimed claim 1, wherein detection sensitivities of the test strip 1 and the test strip 2 both are 50 international units per milliliter (IU/mL) determined by quantification using a sheep brucellosis positive standard serum with a content of 1,000 IU/mL.

5. The antibody detection test strip of integrating primary screening and diagnosis of sheep brucellosis as claimed claim 4, wherein a method for quantification of the detection sensitivities of the test strip 1 and the test strip 2 comprises:

diluting the sheep brucellosis positive standard serum with physiological saline at four different dilution ratios of 1:10, 1:20, 1:40 and 1:80, namely contents of serum antibody being 100 IU/mL, 50 IU/mL, 25 IU/mL and 12.5 IU/mL; dripping each of positive serums with the respective dilution ratios two drops (100 μL) into the sample-loading hole, and reading results within 2~5 minutes; and determining results of detection sensitivities of the test strip 1 and the test strip 2 as that: for the sheep brucellosis positive standard serum diluted as 1:20, namely 50 IU/mL, it is determined as positive because that a test line of the test strip 1 presents no band but a control line of the test strip 1 presents a band, and a test line and a control line of the test strip 2 each present a band; and for the sheep brucellosis positive standard serum diluted as 1:40, namely 25 IU/mL, it is determined as negative because that the test line and the control line of the test strip 1 each present a band, and the test line of the test strip 2 presents no band but the control line of the test strip 2 presents a band.

6. The antibody detection test strip of integrating primary screening and diagnosis of sheep brucellosis as claimed claim 1, wherein when the antibody detection test strip of integrating primary screening and diagnosis of sheep brucellosis in use, what are performed as follows:

(1) sample processing: taking whole blood of an animal sheep, and separating a sheep serum, wherein the sheep serum is clear and free of hemolysis;

(2) operation method: dripping two drops (100 μL) of the sheep serum into the sample-loading hole, and reading a result within 2-5 minutes; and (3) criteria of determination: determining as brucellosis negative (−) when a test line and a control line of the test strip 1 each present a band, and a test line of the test strip 2 presents no band but a control line of the test strip 2 presents a band; determining as brucellosis positive (+) when the test line of the test strip 1 presents no band but the control line of the test strip 1 presents a band, and the test line and the control line of the test strip 2 each present a band; determining as brucellosis suspicious (±) when the test line of the test strip 1 presents no band but the control line of the test strip 1 presents a band, and the test line of the test strip 2 presents no band but the control line of the test strip 2 presents a band; or, determining as invalid when the control line of each of the test strip 1 and the test strip 2 presents no band.

\* \* \* \* \*